Figure 1:
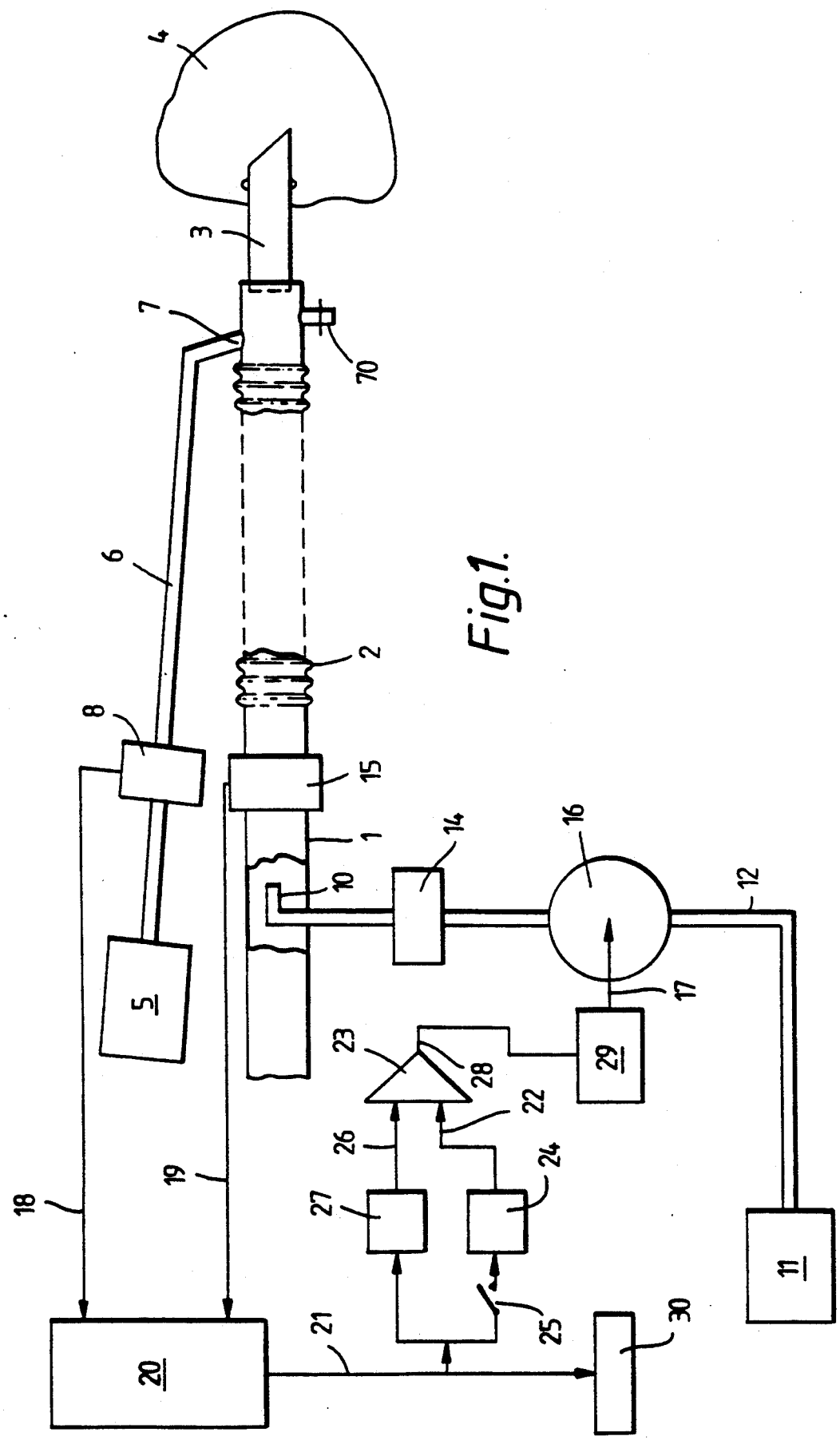

United States Patent [19]

Whitwam et al.

[11] Patent Number: 5,307,795
[45] Date of Patent: May 3, 1994

[54] MEDICAL VENTILATORS

[75] Inventors: James G. Whitwam, London; Mihir K. Chakrabarti, Greenford, both of England

[73] Assignee: Caduceus Limited, London, England

[21] Appl. No.: 778,131

[22] PCT Filed: Jun. 5, 1990

[86] PCT No.: PCT/GB90/00870

§ 371 Date: Jan. 24, 1992

§ 102(e) Date: Jan. 24, 1992

[87] PCT Pub. No.: WO90/14852

PCT Pub. Date: Dec. 13, 1990

[30] Foreign Application Priority Data

Jun. 7, 1989 [GB] United Kingdom ............... 8913085

[51] Int. Cl.$^5$ ........................................... A61M 16/00
[52] U.S. Cl. ........................ 128/204.25; 128/204.24; 128/204.23
[58] Field of Search ............... 128/204.18, 204.21, 128/204.23, 725, 204.24, 204.25

[56] References Cited

U.S. PATENT DOCUMENTS

| 1,214,941 | 2/1917 | Morris et al. | 128/204.25 |
|---|---|---|---|
| 3,485,243 | 12/1969 | Bird et al. | 128/204.25 |
| 3,741,208 | 6/1973 | Jonsson et al. | 128/204.21 |
| 3,961,627 | 6/1976 | Ernst et al. | 128/204.21 |
| 3,976,064 | 8/1976 | Wood et al. | 128/204.21 |
| 4,471,773 | 9/1984 | Bunnell et al. | 128/204.21 |
| 4,481,944 | 11/1984 | Bunnell | 128/204.18 |
| 4,495,946 | 1/1985 | Lemer | 128/204.25 |
| 4,520,812 | 6/1985 | Freitag et al. | 128/204.25 |
| 4,537,190 | 8/1985 | Caillot et al. | 128/204.22 |
| 4,596,247 | 6/1986 | Whitwam et al. | 128/204.25 |
| 4,957,107 | 9/1990 | Sipin | 128/204.21 |
| 4,971,049 | 11/1990 | Rotarin et al. | 128/204.21 |
| 5,107,830 | 4/1992 | Younes | 128/204.23 |

FOREIGN PATENT DOCUMENTS

| 0082041 | 6/1983 | European Pat. Off. . |
|---|---|---|
| 0080155 | 11/1984 | European Pat. Off. . |
| 0234736 | 9/1987 | European Pat. Off. . |
| 309595 | 3/1916 | Fed. Rep. of Germany . |
| 2221152 | 11/1974 | France . |
| 2117648A | 10/1983 | United Kingdom . |
| 2137887A | 10/1984 | United Kingdom . |

Primary Examiner—David A. Wiecking
Assistant Examiner—Aaron J. Lewis
Attorney, Agent, or Firm—Klarquist Sparkman Campbell Leigh & Whinston

[57] ABSTRACT

A medical ventilator comprises a ventilator duct having an inlet for respiratory fresh gas. The pressure at which the respiratory fresh gas is supplied to the patient is determined by a driving jet disposed in the ventilator duct at a distance from the inlet so that an intervening column of gas acts as a pneumatic piston. The supply of driving gas to the jet is initially set by a regulator to obtain a desired value of a respiratory parameter, such as the volume of gas ventilating the patient's lungs during the breathing cycle. The volume of gas expelled from the patient's lungs is monitored during operation by detecting means and the regulator is adjusted by a servomotor in response to any change in the measured parameter in order to maintain the parameter at the desired value.

10 Claims, 2 Drawing Sheets

MEDICAL VENTILATORS

This invention relates to improvements in or relating to medical ventilators and, in particular, concerns improvements in the control of the operation of medical ventilators.

There are two basic types of known medical ventilators.

A first known kind of medical ventilator, termed a constant volume flow generator, operates with respiratory fresh gas at relatively high pressure and therefore functions as a flow generator capable of providing a set flow of respiratory fresh gas such that the volume of respiratory gas supplied to a patient during a breathing cycle remains approximately constant irrespective of changes in the pulmonary characteristics, i.e. resistance of the airways and pulmonary compliance, which constitute a load to the ventilator. This type of ventilator is not versatile for all age groups of patients and suffers from high lung pressures.

A second known kind of medical ventilator operates with a relatively low generated pressure and functions as a pressure generator which is not capable of maintaining constant the volume of the ventilating respiratory gas supplied to the patient during a breathing cycle in the face of changes in the pulmonary characteristics. This pressure generator type of ventilator is highly versatile and can be used safely for any patient age groups.

Because known medical ventilators of the second kind are preset to maintain pressure conditions which are constant once set, changes in the condition of the lungs of a patient connected to such a ventilator, after the initial pressure conditions have been set to suite the initial condition of the patient's lungs, can cause considerable changes in physiological respiratory parameters, such as the volume of gas delivered to the patient's lungs during the breathing cycle or the concentration of carbon dioxide in the expired gas at the end of the expiration phase of the breathing cycle, the so-called end tidal carbon dioxide concentration.

It is an object of the present invention to provide an improved medical ventilator of the pressure generator kind and a method of operating such a ventilator to regulate automatically a selected physiological parameter of the patient's respiration, even though the pulmonary characteristics change over time.

Accordingly, in one aspect, the present invention provides a medical ventilator comprising means for initially setting the pressure of respiratory fresh gas supplied to a patient to obtain a desired value of a respiratory parameter to be controlled, means for measuring the value of the respiratory parameter during subsequent operation of the ventilator, means for detecting in the measured value of the respiratory parameter any change from the desired value, and means for adjusting the setting means in dependent upon the change in the measured value of the respiratory parameter in order to vary the pressure of respiratory fresh gas supplied by the ventilator so as to maintain the respiratory parameter at the desired value.

In another aspect, the invention provides a method of operating a medical ventilator in which the pressure of respiratory fresh gas supplied to a patient is variable, comprising initially setting the pressure of the respiratory fresh gas to obtain a desired value of a respiratory parameter to be controlled, measuring the respiratory parameter during subsequent operation of the ventilator, detecting in the measured respiratory parameter any change from the desired value, and adjusting the pressure of the respiratory fresh gas supplied by the ventilator in dependence upon the change in the respiratory parameter so as to maintain the respiratory parameter at the desired value.

Figure 2:
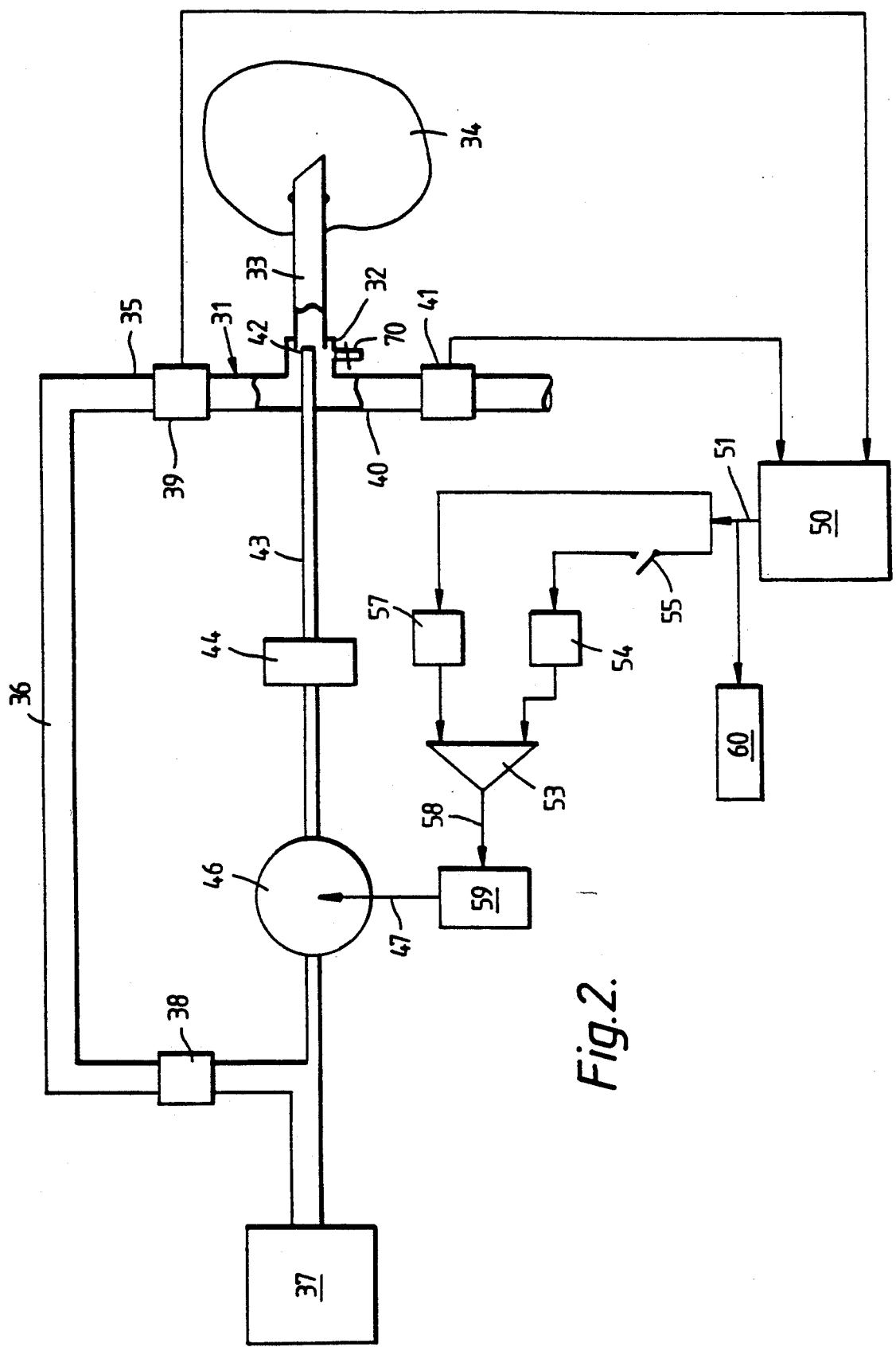

In order that the invention may be more readily understood, embodiments thereof will now be described, by way of example, with reference to the accompanying drawings, in which:

FIG. 1 is a diagrammatic representation of one medical ventilator embodying the present invention; and FIG. 2 is a diagrammatic representation of another medical ventilator embodying the invention.

Referring firstly to FIG. 1, one embodiment of a medical ventilator according to the present invention comprises a ventilator duct 1 having a flexible patient tube 2 by which the duct 1 is connected to a tracheal tube 3 for insertion into the airway of a patient 4.

A source 5 of respiratory gas at relatively low pressure is connected by a respiratory fresh gas conduit 6, which is relatively narrow compared to the ventilator duct, to an inlet 7 at the patient end of the patient tube 2 adjacent the proximal end of the tracheal tube 3. A continuous flow of respiratory gas is supplied through the conduit 6 during operation of the ventilator and a flow sensor 8 in the fresh gas conduit 6 is arranged to measure the volume of respiratory fresh gas supplied through the conduit 6 during the expiratory phase of each breathing cycle.

A driving gas jet 10 is located in the ventilator duct 1 and is connected to a source 11 of high pressure driving gas, which may or may not be the same as the respiratory fresh gas by a supply line 12. A solenoid valve 14 is incorporated in the supply line 12 and is controlled by an electrical pulse generator (not shown) to act as a chopper to supply pulses of high pressure gas to the jet 10 which is orientated to deliver the driving gas axially into the ventilator duct 1 towards the patient end thereof, so as to impose a cyclically varying pressure on the low pressure respiratory gas delivered at inlet 7 through the fresh gas conduit 6. The distance between the inlet 7 and the jet 10 is such that the column of gas in the ventilator duct between the jet 10 and the inlet 7 acts as a pneumatic piston to impose the required pressure variation on the respiratory fresh gas delivered at inlet 7 without the driving gas itself taking part in the respiration process.

The gas emerging from the patient's lungs during the expiration phase of the breathing cycle passes out of the ventilator, together with the fresh gas supplied to inlet 7 during the expiration phase, through the relatively wide ventilator duct 1. A flow sensor 15 is incorporated in the ventilator duct and is arranged to measure the total expired volume composed of the volume of gas expelled from the patient's lungs and the volume of respiratory fresh gas supplied during the expiration phase.

A regulator 16, which may be either a flow regulator or a pressure regulator, is connected in the supply pipe 12 between the solenoid valve 14 and the driving gas source 11 and has a control member 17 which is adjustable manually to vary either the flow rate or the pressure of the gas supplied to the solenoid valve 14. The flow sensors 8 and 15 deliver respective electrical measurement signals which are significant of the volume of fresh gas supplied through the fresh gas supply duct 6 during the expiration phase of breathing in the case of sensor 8 and of the total volume of gas passing through the ventilator duct 1 during the expiration phase in the case of sensor 15. The electrical measurement signals are supplied on lines 18 and 19 to a subtracting circuit 20 which establishes the difference between the signals delivered by the two sensors 8 and 15. The resultant electrical measurement signal delivered at the output 21 of the subtracting circuit 20 is significant of the volume of gas expelled from the patient's lungs during the expiration phase of breathing and corresponds to the volume of gas ventilating the patient's lungs, i.e. the so-called expired tidal volume. The signal at the output 21 of circuit 20 is delivered to a first input 22 of a comparator 23 via a reference memory 24 which is connected to the output 21 by a normally closed isolating switch 25 (shown however in its open condition). The output 21 of the comparator 20 is also connected to a second input 26 of the comparator 23 via a current value memory 27. An output 28 of the comparator 23 is connected to a servo motor 29 which acts to adjust the control member 17 of the regulator 16. The output 21 of the subtracting circuit 20 may also be connected to a display device 30 for displaying the measured value of the ventilating volume.

In use of the ventilator described above with reference to FIG. 1, the control member 17 of the regulator 16 is initially manually adjusted at the start of ventilation to deliver a desired value of the volume of gas to the patient's lungs and which it is desired to maintain for the patient under ventilation regardless of changes in the patient's condition. Once the desired value of the ventilating volume has been achieved, the isolating switch 25 is opened to disconnect the reference memory 24 from the subtracting 20, so that the memory 24 now stores a fixed reference value of the resultant measurement signal corresponding to the desired set ventilating volume and delivers a signal corresponding to this reference value to the input 27 of the comparator 23. The current value memory 27 continues, however, to be updated with the new value of the resultant measurement signal which is delivered at the output of the subtracting circuit 20 at the end of each expiration phase of the breathing cycle and delivers a signal corresponding to the updated current value to the input 26 of the comparator 23. If the ventilating volume subsequently changes from the desired set value as a result, for example, of changes in the compliance of the patient's lungs, the signals applied to inputs 22 and 26 of the comparator 23 become different and the comparator delivers an error signal on output 28 to the servo motor 29 which operates to adjust the control member 17 in the required sense to restore the ventilating volume to its desired preset value.

Another embodiment of a medical respirator according to the present invention is illustrated diagrammatically in FIG. 2 of the drawings and comprises a T-shaped ventilator duct 31 having a stem portion 32 coupled to the proximal end of a tracheal tube 33 for insertion in the airway of a patient 34.

A first branch 35 of the ventilator duct 31 has its end connected to a respiratory fresh gas conduit 36 connected to a high pressure source 37 of repiratory fresh gas. The respiratory fresh gas flowing through the fresh gas duct 36 is regulated to a relative low pressure by a flow regulator 38. The branch 35 of the ventilator duct is provided with a flow sensor 39 arranged to measure the volume of fresh gas supplied through the branch 35 during the expiration phase of the breathing cycle.

The other branch 40 of the ventilator duct 31 has its end open and incorporates a flow sensor 41 arranged to measure the total volume of gas passing through the branch 40 during the expiration phase of the breathing cycle, this total expired volume being composed of the volume of gas expelled from the lungs of the patient, i.e. the volume of gas ventilating the patient's lungs, and the volume of fresh gas supplied through branch 35 during the expiration phase.

A driving jet 42 is positioned in the ventilator duct 31 and is supplied with driving gas by a driving gas line 43 connected to the high pressure source 37 of respiratory fresh gas. The driving gas supply line contains a solenoid valve 44 and a flow or pressure regulator 46 having a control member 47 which is manually settable and adjustable by a servomotor 59 under the control of a control circuit which is similar to that of FIG. 1 and comprises a subtracting circuit 50 receiving respective measurement signals from flow sensors 39 and 41 on lines 48 and 49, a reference memory 54 connected to output 51 of circuit 50 via isolating switch 55, a current value memory 57 connected permanently to output 51, comparator 53 having its output 58 connected to the servomotor 59, and a display device 60.

In the embodiment described with reference to FIG. 2, the low pressure respiratory gas is supplied continuously through the conduit 36 during operation of the ventilator. The solenoid 44 delivers pulses of respiratory fresh gas to the jet 42 which thus emits a cyclically varying flow of relatively high pressure respiratory gas which entrains into the stem 32 of the ventilator duct the lower pressure respiratory gas supplied through the branch 35 of the ventilator duct during the inspiration phase of breathing. During the expiration phase of breathing, the gases expelled from the patient's lungs are delivered through the open branch 40 of the ventilator duct together with the low pressure respiratory fresh gas which continues to flow through the branch 35 of the ventilator duct.

In use of the FIG. 2 ventilator to maintain the volume of gas ventilating from the patient's lungs at a desired preset level, the control member 46 of the regulator 45 is initially adjusted until the desired ventilating volume is achieved and the isolating switch 55 is then opened so that the servomotor 59 is controlled in accordance with the comparison of the reference value stored in reference memory 54 and the updated current value stored in the current value memory 57 in order to maintain the ventilating volume at a constant level.

Although the above embodiments of the invention have been described with reference to the maintenance of a desired value of the volume of gas ventilating the lungs of the patient, it is envisaged that the ventilator may be arranged to maintain any other appropriate parameter of the respiration process by providing suitable sensing means to detect the current value of the parameter to be maintained during operation of the ventilator. For example, the concentration of carbon dioxide at the end of the expiration phase, i.e. the end tidal carbon dioxide concentration, could be controlled to a desired value by providing a suitable carbon dioxide detector 70, such as a known infra red carbon dioxide detector, to measure the carbon dioxide concentration in the vicinity of the proximal end of the tracheal tube 3 or 33 at the relevant instant in the breathing cycle. The electrical output from the carbon dioxide detector could then be applied to the reference memory and the current value memory in place of or instead of the output signal of the subtracting circuit 20 or 50.

We claim:

1. A method of operating a medical ventilator to generate a variable pressure in the airways of a patient, with respiratory fresh gas being continuously delivered during an expiration phase of each breathing cycle, comprising the steps of:

initially setting the pressure to obtain a desired value of the volume of gas ventilating the lungs of the patient, which value is to be controlled;

measuring the total volume of expired gas flowing in the ventilator away from the patient during the expiration phase;

measuring the volume of respiratory fresh gas delivered by the ventilator during the expiration phase;

subtracting the measured volume of respiratory fresh gas from the measured total volume of expired gas to calculate the volume of gas expelled from the lungs of the patient;

detecting in the calculated value of the volume of gas ventilating the lungs of the patient any change from the desired value; and adjusting the pressure generated by the ventilator in response to the change in the value of the volume of gas ventilating the lungs of the patient so as to maintain the volume of gas ventilating the lungs of the patient at the desired value.

2. A method according to claim 1 wherein:

the method further includes the step of measuring the concentration of carbon dioxide in the total volume of expired gas; and wherein the adjusting step comprises adjusting the pressure generated by the ventilator in response to the step of measuring the carbon dioxide concentration.

3. A medical ventilator, comprising:

a controller for initially setting the pressure of respiratory fresh gas, which is continuously supplied, to obtain a desired value of the volume of gas expelled from the lungs of a patient during an expiration phase of a breathing cycle, which value is to be controlled;

a measuring apparatus for measuring the value of the volume of gas expired from the lungs of the patient during subsequent operation of the ventilator comprising:

a first measuring device arranged to measure the total volume of expired gas flowing away from the patient in the ventilator during the expiration phase, the first measuring device generating a first measurement signal in response to the measured total volume;

a second measuring device arranged to measure the volume of respiratory fresh gas delivered by the ventilator during the expiration phase, the second measuring device generating a second measurement signal in response to the measured volume of respiratory fresh gas; and a subtracting device for subtracting the second measurement signal from the first measurement signal to generate a resultant measurement signal significant of the volume of gas expelled from the lungs of the patient;

a detector responsive to the resultant measurement signal for detecting any change in the measured value of the volume of gas expired from the lungs of the patient from the desired value; and an adjustment device for adjusting the controller in response to a detected change in the measured value of the volume of gas expired from the lungs of the patient in order to vary the pressure of respiratory fresh gas supplied by the ventilator so as to maintain the volume of gas expired from the lungs of the patient at the desired value.

4. A ventilator according to claim 3, further comprising:

a reference memory to which the resultant measurement signal is delivered via a normally closed isolating switch which is opened upon setting of the desired value of the volume of gas expired from the lungs of the patient to store an initial reference value of the resultant measurement signal in the reference memory;

a current value memory which is permanently connected to receive the resultant measurement signal from the subtracting device;

a comparator for comparing the contents of the reference memory and the current value memory during operation of the ventilator and delivering an output error signal significant of any difference between the contents of the reference memory and the current value memory; and a servomotor connected to receive the error signal from the comparator and coupled to adjust the setting device of the ventilator in response to the error signal.

5. A ventilator according to claim 3 wherein the setting device is arranged to control the supply of driving gas to a driving jet which is disposed in a ventilator duct of the ventilator and to determine the pressure of respiratory gas supplied to the patient.

6. A ventilator according to claim 5, wherein the setting device is a flow regulator or a pressure regulator via which the high pressure driving gas is delivered to the driving jet.

7. A ventilator according to claim 5, comprising the inlet at a patient end of the ventilator duct for connection to a source of respiratory fresh gas, the driving jet being so spaced from the respiratory gas inlet that a column of gas in the respirator duct between the driving jet and the inlet acts as a pneumatic piston to transmit pressure from the driving gas to the flow of respiratory fresh gas supplied to the patient end of the ventilator duct.

8. A ventilator according to claim 5, wherein the ventilator duct comprises a stem having a base which splits into first and second branches, the base for connection to a patient, the first branch for connection to a source of respiratory fresh gas and the second branch through which expired gas flows during an expiration phase of a breathing cycle, with the jet being disposed in the stem of the ventilator duct so as to entrain respiratory fresh gas from the first branch of the ventilator duct during an inspiration phase of the breathing cycle.

9. A ventilator according to claim 4, further including a measuring device for measuring the concentration of carbon dioxide in the total volume of expired gas.

10. A ventilator according to claim 3 wherein:

the setting device is arranged to control the supply of driving gas to a driving jet which is disposed in a ventilator duct of the ventilator and to determine the pressure of respiratory gas supplied to the patient;

the ventilator duct comprises a stem having a base which splits into first and second branches, the base for connection to a patient, the first branch for connection to a source of respiratory fresh gas and the second branch through which expired gas flows during an expiration phase of a breathing cycle, with the jet being disposed in the stem of the ventilator duct so as to entrain respiratory fresh gas from the first branch of the ventilator duct during an inspiration phase of the breathing cycle;

the ventilator further comprises an inlet at a patient end of the ventilator duct for connection to a source of respiratory fresh gas;

the driving jet is spaced from the respiratory gas inlet that a column of gas in the respirator duct between the driving jet and the inlet acts as a pneumatic piston to transmit pressure from the driving gas to the flow of respiratory fresh gas supplied to the patient end of the ventilator duct; and the ventilator further comprises a measuring device for measuring the concentration of carbon dioxide in the total volume of expired gas.

* * * * *